United States Patent [19]

Farge et al.

[11] 4,064,247

[45] Dec. 20, 1977

[54] THIAZOLO[3,4-B]ISOQUINOLINE DERIVATIVES AND PHARMACEUTICAL COMPOSITIONS CONTAINING THEM

[75] Inventors: Daniel Farge, Thiais; Alain Jossin, Saint Cloud; Gérard Ponsinet, Sucy-En-Brie; Daniel Reisdorf, Thiais, all of France

[73] Assignee: Rhone-Poulenc Industries, Paris, France

[21] Appl. No.: 711,963

[22] Filed: Aug. 5, 1976

[30] Foreign Application Priority Data

Aug. 6, 1975 France .............................. 75.24523
May 18, 1976 France .............................. 76.14935

[51] Int. Cl.² .................... C07D 513/14; A61K 31/47
[52] U.S. Cl. .............................. 424/258; 260/288 CF; 260/283 S; 260/283 CN; 260/289 C; 260/289 D; 260/287 D; 260/286 R; 260/283 R; 260/294.8 R
[58] Field of Search ...... 260/283 S, 288 CF, 283 CN; 424/258

[56] References Cited

U.S. PATENT DOCUMENTS 3,455,933 7/1969 Georgiadis et al. ................. 260/289
3,979,397 9/1976 Harsanyi et al. .............. 260/288 CF Primary Examiner—Donald G. Daus
Assistant Examiner—D. G. Rivers
Attorney, Agent, or Firm—Stevens, Davis, Miller & Mosher

[57] ABSTRACT

Thiazolo[3,4-b]isoquinoline derivatives of the general formula:

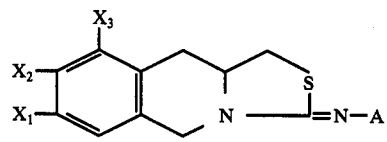

wherein A represents 3-pyridyl, 4-pyridyl or 5-isoquinolyl and, when A represents 3-pyridyl, $X_1$ represents hydrogen, halogen, dimethylamino or cyano, $X_2$ represents hydrogen or fluorine and $X_3$ represents hydrogen or nitro, at least two of $X_1$, $X_2$ and $X_3$ representing hydrogen, or $X_1 X_2$ together represent methylenedioxy and $X_3$ represents hydrogen, and when A represents 4-pyridyl or 5-isoquinolyl, $X_1$, $X_2$ and $X_3$ each represent hydrogen, and non-toxic pharmaceutically acceptable acid addition salts thereof, possess useful pharmacodynamic properties, in particular analgesic and antipyretic activity.

18 Claims, No Drawings

THIAZOLO[3,4-B]ISOQUINOLINE DERIVATIVES AND PHARMACEUTICAL COMPOSITIONS CONTAINING THEM

This invention relates to new therapeutically useful thiazolo[3,4-b]isoquinoline derivatives, to processes for their preparation and to pharmaceutical compositions containing them.

The new thiazolo[3,4-b]isoquinoline derivatives of the present invention are those of the general formula:

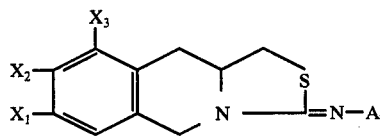

(I)

wherein A represents a heterocyclic radical containing one nitrogen atom, selected from 3-pyridyl, 4-pyridyl and 5-isoquinolyl and, when A represents a 3-pyridyl radical, $X_1$ represents a hydrogen or halogen atom, or a dimethylamino or cyano radical, $X_2$ represents a hydrogen or fluorine atom and $X_3$ represents a hydrogen atom or a nitro radical, at least two of $X_1$, $X_2$ and $X_3$ representing hydrogen atoms, or $X_1$ and $X_2$ together represent a methylenedioxy radical and $X_3$ represents a hydrogen atom, and when A represents a 4-pyridyl or 5-isoquinolyl radical $X_1$, $X_2$ and $X_3$ each represent a hydrogen atom, and acid addition salts thereof.

The compounds of general formula I can exist in (R)- and (S)- forms and the invention includes both such forms and mixtures thereof.

According to a feature of the present invention the thiazolo[3,4-b]isoquinoline derivatives of general formula I are prepared by one of the following processes:

1. Compounds of general formula I wherein A represents a 3-pyridyl or 5-isoquinolyl radical and when A represents a 3-pyridyl radical, $X_1$ represents a hydrogen or halogen atom, $X_2$ represents a hydrogen or fluorine atom, $X_3$ represents a hydrogen atom or a nitro radical, at least two of $X_1$, $X_2$ and $X_3$ representing hydrogen atoms, or $X_1$ and $X_2$ together represent a methylenedioxy radical and $X_3$ represents a hydrogen atom, and when A represents a 5-isoquinolyl radical, $X_1$, $X_2$ and $X_3$ represent hydrogen atoms, are prepared by cyclisation of a 1,2,3,4-tetrahydroisoquinoline derivative of the general formula:

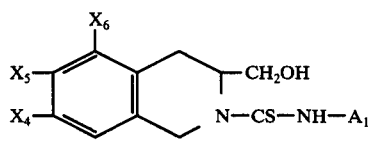

II wherein $A_1$ represents a 3-pyridyl or 5-isoquinolyl radical and, when $A_1$ represents a 3-pyridyl radial, $X_4$ represents a hydrogen or halogen atom, $X_5$ represents a hydrogen or fluorine atom, $X_6$ represents a hydrogen atom or a nitro radical, at least two of $X_4$, $X_5$ and $X_6$ representing hydrogen atoms, or $X_4$ and $X_5$ togther represent a methylenedioxy radical and $X_6$ represents a hydrogen atom, and when $A_1$ represents a 5-isoquinolyl radical $X_4$, $X_5$ and $X_6$ represent hydrogen atoms.

The reaction is generally carried out by heating in an acid medium. It is particularly advantageous to carry out the reaction at a temperature from 65° to 100° C. in an aqueous inorganic acid, for example in hydrochloric acid.

The 1,2,3,4-tetrahydroisoquinoline derivatives of general formula II can be obtained by reacting an isothiocyanate of the general formula:

III (wherein $A_1$ is as hereinbefore defined), with a 3-hydroxymethyl-1,2,3,4-tetrahydroisoquinoline derivative of the general formula:

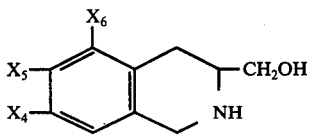

IV wherein $X_4$, $X_5$ and $X_6$ are as hereinbefore defined. The reaction is generally carried out in an organic solvent such as an alcohol, for example ethanol, at a temperature from 15° to 70° C.

The isothiocyanate of general formula III wherein $A_1$ represents a 3-pyridyl radical can be prepared in accordance with the method described by J. C. Jochims, Chem. Ber. 101, 1746 (1968).

The isothiocyanate of general formula III wherein $A_1$ represents a 5-isoquinolyl radical can be obtained by condensing carbon disulphide with 5-aminoisoquinoline, followed by addition of dicyclohexylcarbodiimide. The condensation is generally carried out in the presence of a base such as a tertiary amine, for example triethylamine. The reaction is advantageously carried out in an organic solvent, such as pyridine, at a temperature from −10° to 25° C.

The 3-hydroxymethyl-1,2,3,4-tetrahydroisoquinoline derivatives of general formula IV can be obtained by reduction of a 1,2,3,4-tetrahydroisoquinoline derivative of the general formula:

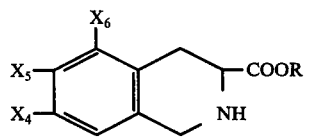

V (wherein R represents a hydrogen atom or an alkyl radical containing from 1 to 4 carbon atoms and $X_4$, $X_5$ and $X_6$ are as hereinbefore defined) or of an acid addition salt thereof.

When R in general formula V represents a hydrogen atom, the reduction is preferably carried out using lithium aluminium hydride, in tetrahydrofuran, at a temperature from 20° to 70° C.

When R in general formula V represents an alkyl radical containing from 1 to 4 carbon atoms, the reduction is preferably caried out by means of an alkali metal borohydride, such as sodium borohydride, in an organic solvent or an aqueous-organic medium, such as an ethanol-water mixture, and at a temperature from 10° C. to the reflux temperature of the reaction mixture.

When a product of general formula IV in which $X_6$ represents a nitro radical is required it is preferable to use an ester of general formula V (R = alkyl), the reduction of which takes place under conditions which do not affect the nitro radical.

The 1,2,3,4-tetrahydroisoquinoline derivatives of general formula V, wherein R represents an alkyl radical containing 1 to 4 carbon atoms, can be obtained by esterification of a 1,2,3,4-tetrahydroisoquinoline derivative of general formula V, wherein R represents a hydrogen atom, by known methods for the conversion of an acid into an ester without affecting the rest of the molecule.

By the term "known methods" as used in this Specification and accompanying claims is meant methods heretofore used or described in the chemical literature.

The 1,2,3,4-tetrahydroisoquinoline derivatives of general formula V wherein R represents a hydrogen atom, $X_4$ and $X_5$ are as hereinbefore defined and $X_6$ represents a hydrogen atom can be obtained from a phenylalanine derivative of the general formula:

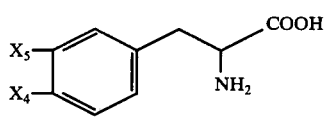

VI (wherein $X_4$ and $X_5$ are as hereinbefore defined) by application of the method described by A. Pictet and Th. Spengler, Chem. Ber., 44, 2030 (1911).

When the L-form of a phenylalanine derivative of general formula VI is used, the product of general formula I obtained via the compound of general formula V is in the (S)-form. When a phenylalanine derivative of general formula VI in the D-form is used the product of general formula I is obtained in the (R)-form. When a mixture of the D- and L-forms of the phenylalanine derivative of general formula VI is used, the product of general formula I is obtained in the (R,S)-form.

The compounds of general formulae II, IV and V wherein the symbol $X_6$ represents a nitro radical can be obtained by nitration of a compound of general formula II, IV or V wherein $X_6$ represent a hydrogen atom. The nitration is generally carried out by means of a mixture of nitric and sulphuric acid at a temperature of about $-20°$ C. or with a mixture of sodium nitrate and trifluoroacetic acid at a temperature of about 20° C., followed, if desired, by separation of the isomers obtained.

2. Compounds of general formula I wherein $X_1$ represents a hydrogen or halogen atom or a cyano radical and A, $X_2$ and $X_3$ are as hereinbefore defined are prepared by reaction of an amine of the general formula:

$H_2N - A$    VII (wherein A is as hereinbefore defined) with a salt of the general formula:

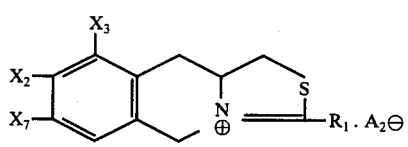

VIII wherein $X_7$ represents a hydrogen or halogen atom or a cyano radical, $R_1$ represents a chloride atom, an alkylthio radical containing 1 to 4 carbon atoms (preferably a methylthio radical) or a benzylthio radical, $A_2^-$ represents an anion, such as a chloride, iodide, sulphate, tetrafluoroborate or fluorosulphonate ion, and $X_2$ and $X_3$ are as hereinbefore defined. When $R_2$ represents a chlorine atom, $A_2^-$ represents a chloride ion. When $R_1$ represents an alkylthio or benzylthio radical $A_2^-$ represents an anion such as an iodide, sulphate tetrafluoroborate or fluorosulphonate ion.

When $R_1$ represents a chlorine atom and $A_1^-$ represents a chloride ion, the reaction is preferably carried out in an organic solvent, such as acetonitrile, in the presence of an alkaline condensation agent, such as triethylamine, at a temperature of about 20° C.

When $R_1$ represents an alkylthio or benzylthio radical and $A_2^-$ represents an iodide, sulphate, tetrafluoroborate or fluorosulphonate ion, the reaction is preferably carried out in a basic organic solvent, such as pyridine, at a temperature of about 20° C.

The salt of general formula VIII wherein $R_1$ represents a chlorine atom and $A_2^-$ represents a chloride ion can be obtained by the reaction of a chlorinating agent, such as phosgene, phosphorus pentachloride, thionyl chloride or oxalyl chloride on a thiazolo[3,4-b]isoquinoline-3-thione derivative of the general formula:

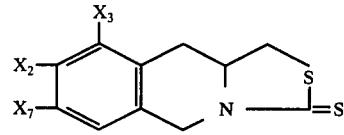

IX wherein $X_2$, $X_3$ and $X_7$ are as hereinbefore defined. The reaction is generally carried out in an organic solvent or a mixture of organic solvents, such as a mixture of toluene and tetrahydrofuran, at a temperature from 0° to 70° C.

The salts of general formula VIII wherein $R_1$ represents an alkylthio or benzylthio radical and $A_2^-$ represents an iodide, sulphate, tetrafluoroborate or fluorosulphonate ion can be obtained by the reaction of a reactive ester of the general formula:

$R_2 - A_2$    X (wherein $R_2$ represents an alkyl radical containing from 1 to 4 carbon atoms or a benzyl radical and $A_2$ represents the residue of a reactive ester such as an iodine atom, or an alkoxysulphonyloxy radical) or of triethyloxonium tetrafluoroborate or methyl fluorosulphonate and a compound of general formula IX. The reaction is generally effected, optionally in the presence of an organic solvent such as methylene chloride, at a temperature of about 20° C.

The thiazolo[3,4-b]isoquinoline-3-thione derivatives of general formula IX wherein $X_2$, $X_3$ and $X_7$ are as hereinbefore defined (with the exception of those derivatives wherein $X_7$ represents a cyano radical) can be obtained by the reaction of carbon disulphide, in a basic medium, with an isoquinoline derivative of the general formula:

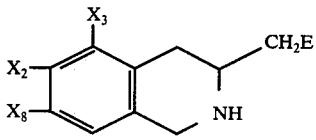

XI wherein $X_8$ represents a hydrogen or halogen atom, E represents a halogen, e.g. bromine or chlorine, atom or a hydroxysulphonyloxy radical, and $X_2$ and $X_3$ are as hereinbefore defined. The reaction is generally carried out in the presence of sodium or potassium hydroxide at a temperatue of about 20° C.

Compounds of general formula XI can be obtained by the action of an inorganic acid on a 3-hydroxymethylisoquinoline derivative of general formula IV wherein $X_5$ and $X_6$ are as hereinbefore defined and $X_4$ represents a hydrogen or halogen atom. Compounds of general formula XI wherein E represents a hydroxysulphonyloxy radical are generally prepared by treatment of the derivative of general formula IV with sulphuric acid in an aqueous medium at a temperature of about 100° C., or in an organic solvent (such as dimethylformamide) in the presence of dicyclohexylcarbodiimide at a temperature of about 20° C.

Compounds of general formula XI wherein E represents a bromine atom are generally prepared by treatment of the derivative of general formula IV with aqueous hydrobromic acid (48% w/v) at the reflux temperature of the reaction medium, and isolating the product of general formula XI as its hydrobromide.

Compounds of general formula XI wherein E represents a chlorine atom, are generally prepared by treatment of the derivative of general formula IV with thionyl chloride in an organic solvent, such as chloroform, saturated with hydrogen chloride gas, and at the reflux temperature of the reaction mixture and isolating the product of general formula XI as its hydrochloride.

Compounds of general formula IX or XI, wherein $X_3$ represents a nitro radical, can also be obtained by nitration of a compound of general formula IX or XI wherein $X_3$ represents a hydrogen atom. The nitration is generally carried out with a mixture of nitric and sulphuric acid at a temperature of about $-20°$ C., or with nitronium fluoroborate in acetonitrile at a temperature of about 20° C., or with sodium nitrate in trifluoroacetic acid at a temperature of about 20° C., followed, if desired, by separation of the isomers obtained.

The compounds of general formula IX wherein $X_7$ represents a cyano radical and $X_2$ and $X_3$ are as hereinbefore defined, can be obtaned from a compound of general formula IX wherein $X_7$ is replaced by a nitro radical, i.e. from a compound of the general formula:

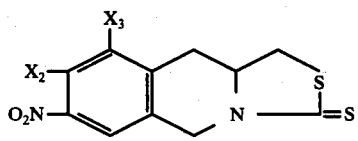

XII (wherein $X_2$ and $X_3$ are as hereinbefore defined) by known methods for the conversion of a nitro radical to a cyano radical, via the corresponding amine intermediate.

Compounds of general formula XII can be obtained from a compound of general formula IX wherein $X_1$ represents a hydrogen atom in accordance with the method hereinbefore described for the preparation of compounds of general formula IX wherein $X_3$ represents a nitro radical from compounds of general formula IX wherein $X_3$ represents a hydrogen atom.

3. Compounds of general formula I wherein A represents a 3-pyridyl radical, $X_1$ represents a hydrogen or halogen atom or a dimethylamino or cyano radical, $X_2$ represents a hydrogen or fluorine atom and $X_3$ represents a hydrogen atom, (wherein $X_1$ and $X_2$ are different and one of them represents a hydrogen atom) are prepared by reducing by methods known per se the nitro radical in a compound of the general formula:

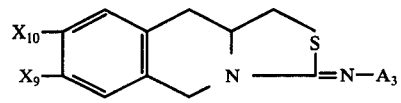

XIII (wherein $A_3$ represents a 3-pyridyl radical, and one of $X_9$ and $X_{10}$ represents a nitro radical and the other represents a hydrogen atom) to obtain a corresponding amino compound of the general formula:

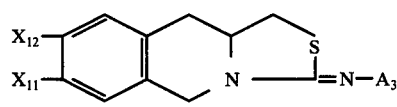

XIV (wherein $A_3$ is as hereinbefore defined and one of $X_{11}$ and $X_{12}$ represents an amino radical and the other represents a hydrogen atom), and conversion of the amino radical in the compound of general formula XIV by methods known per se to a halogen atom, or to a dimethylamino or cyano radical. The reduction of the nitro radical to the amino radical is advantageously carried out in an acid medium (for example hydrochloric acid) in the presence of a metal, such as tin, at a temperature from 10° to 40° C.

Compounds of general formula I wherein $X_1$ represents a chlorine atom, are generally prepared from the compound of general formula XIV obtained as hereinbefore described, by preparation in situ of a diazonium salt in an aqueous medium at a temperture from $-5°$ to $+5°$ C. using sodium nitrite in the presence of an acid (such as hydrochloric acid), and decomposition of the diazonium salt using cuprous chloride at a temperature from 20° to 70° C.

Compounds of general formula I wherein $X_1$ or $X_2$ represents a fluorine atom are generally prepared by decomposition of the diazonium salt prepared as hereinbefore described, at a temperature of about $-10°$ C., using hexafluorophosphoric acid.

Compounds of general formula I wherein $X_1$ represents a cyano radical are generally prepared by decomposition of the diazonium salt prepared as hereinbefore described, using potassium cyanide and copper sulphate. The reaction is advantageously carried out in an aqueous organic medium, for example in a water/toluene mixture, at a temperature from 0° to 50° C.

Compounds of general formula I wherein $X_1$ represents a dimethylamino radical can be obtained from a compound of general formula XIV by treatment with formaldehyde in the presence of a reducing agent. Advantageously sodium cyanoborohydride is used as reducing agent in the presence of an acid such as acetic acid, at a temperature of about 20° C., in an aqueous-organic medium, such as a mixture of water and acetonitrile.

Compounds of general formula XIII wherein $X_9$ and $X_{10}$ are as hereinbefore defined can be obtained from a compound of general formula I wherein A represents a 3-pyridyl radical and $X_1$, $X_2$ and $X_3$ represent hydrogen atoms, by application of the methods hereinbefore described for the preparation of a compound of general formula I wherein A, $X_1$ and $X_2$ are as hereinbefore defined and $X_3$ represents a nitro radical.

The thiazolo[3,4-b]isoquinoline derivatives of general formula I obtained by the aforementioned processes can be purified by physical methods such as crystallisation or chromatography, or by chemical methods such as the formation of salts, crystallisation of the salts and decomposition of them in an alkaline medium. In carrying out the said chemical method the nature of the anion of the salt is immaterial, the only requirement being that the salt must be well-defined and readily crystallisable.

The thiazolo[3,4-b]isoquinoline derivatives of general formula I may be converted by known methods into acid addition salts. The acid addition salts may be obtained by the action of acids on the thiazolo[3,4-b]isoquinoline derivatives in appropriate solvents. As organic solvents there may be used alcohols, ketones, ethers or chlorinated hydrocarbons. The salt which is formed is precipitated, if necessary after concentrating the solution, and is isolated by filtration or by decantation.

The thiazolo[3,4-b]isoquinoline derivatives of general formula I and their acid addition salts possess useful pharmacodynamic properties. They are particularly active as analgesics and antipyretics. They exhibit a slight antiinflammatory activity.

In rats they have proved active as analgesics at doses from 2 to 50 mg./kg., by oral administration, according to the technique of L. O. Randall and J. J. Selitto, Arch. Int. Pharmacodyn. 111, 409 (1957), modified by K. F. Swingle et al., Proc. Soc. Exp. Biol. Med., 137, 536 (1971). The majority of the derivatives have also proved active in mice at doses from 20 to 200 mg./kg., by oral administration, according to the technique of E. Siegmund, Proc. Soc. Exp. Biol. Med. 95, 729 (1957).

The antipyretic activity of the thiazolo[3,4-b]isoquinoline derivatives of general formula I is demonstrated in rats at doses from 5 to 50 mg./kg., by oral administration, according to the technique of J.J. Loux et al., Toxicol. Appl. Pharmacol., 22, 674 (1972).

The anti-inflammatory activity is demonstrated in rats for most of the derivatives at doses from 5 to 50 mg./kg., by oral administration, according to the technique of K. F. Benitz and L. M. Hall, Arch. Int. Pharmacodyn., 144, 185 (1963). In addition, the thiazolo[3,4-b]isoquinoline derivatives of general formula I have low toxicity. The $LD_{50}$ is between 300 mg./kg. and a dose greater than 3,000 mg./kg.

Of particular interest are those thiazolo[3,4-b]isoquinoline derivatives of general formula I wherein A represents a 3-pyridyl, 4-pyridyl or 5-isoquinolyl radical, and $X_1$, $X_2$ and $X_3$ represent a hydrogen atom, in the (R)-and (S)-forms and mixtures thereof, and acid addition salts thereof, more particularly (S)-3-(pyrid-3-ylimino)-1,5,10,10a-tetrahydrothiazolo[3,4-b]isoquinoline, (R)-3-(pyrid-3-ylimino)-1,5,10,10a-tetrahydrothiazolo[3,4-b]isoquinoline, (R,S)-3-(pyrid-3-ylimino)-1,5,10,10a-tetrahydrothiazolo[3,4-b]-isoquinoline, (S)-3-(pyrid-4-ylimino)-1,5,10,10a-tetrahydrothiazolo[3,4-b]isoquinoline, (S)-3-(isoquinol-5-ylimino)-1,5,10,10a-tetrahydrothiazolo[3,4-b]isoquinoline and (R)-3-(isoquinol-5-ylimino)-1,5,10,10a-tetrahydrothiazolo[3,4-b]isoquinoline and acid addition salts thereof.

For therapeutic purposes, the thiazolo[3,4-b]isoquinoline derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllinacetates, salicylates, phenolphthalinates and methylene-bis-β-hydroxynaphthoates) so that the beneficial physiological properties inherent in the bases are not vitiated by side effects ascribable to the anions.

The following Examples illustrate the invention.

EXAMPLE 1

(S)-3-Hydroxymethyl-N-(pyrid-3-yl)-1,2,3,4-tetrahydroisoquinoline-2-carbothioamide (13.5 g.) in 6N hydrochloric acid (300 cc.) is heated for 40 minutes at 100° C. After cooling, the solution obtained is concentrated under reduced pressure (25 mm. Hg) to 1/5 of its volume. It is rendered alkaline by adding 10N sodium hydroxide solution (200 cc.) and is then extracted with methylene chloride (3 × 150 cc.). The organic extracts are combined and then dried over magnesium sulphate. After filtering, and concentrating the filtrate to dryness under reduced pressure (25 mm. Hg), a yellow oil (11 g.) is obtained, which crystallises on addition of diisopropyl ether (150 cc.). The white crystals are filtered off, washed with diisopropyl ether (3 × 10 cc.) and then dried at 60° C., under reduced pressure (1 mm. Hg). (S)-3-Pyrid-3-ylimino)-1,5,10,10a-tetrahydrothiazolo[3,4-b]isoquinoline (9.8 g.), melting at 111° C., is thus obtained.

$[\alpha]_D^{20} = -258 \pm 3°$ ($c = 2$, ethanol).

(S)-3-Hydroxymethyl-N-(pyrid-3-yl)-1,2,3,4-tetrahydroisoquinoline-2-carbothioamide employed as starting material can be prepared in the following manner:

3-Isothiocyanatopyridine (6.8 g.) is added to a solution of (S)-3-hydroxymethyl-1,2,3,4-tetrahydroisoquinoline (8.15 g.) in ethanol (150 cc.). After 3 hours at a temperature of about 20° C., the solution is cooled to 0° C. The white crystals which have appeared are filtered off and are then recrystallised from propanol (200 cc.). After filtration, the crystals are washed with propanol (2 × 10 cc.) and then dried at 60° C. under reduced pressure (1 mm. Hg). (S)-3-Hydroxymethyl-N-(pyrid-3-yl)-1,2,3,4-tetrahydroisoquinoline-2-carbothioamide (12.1 g.) melting at 192° C is thus obtained.

$[\alpha]_D^{20} = +55 \pm 1°$ ($c = 1$, dimethylformamide).

(S)-3-Hydroxymethyl-1,2,3,4-tetrahydroisoquinoline can be prepared in accordance with the method of S. Yamada and T. Kunieda, Chem. Pharm. Bull., 15, 490 (1967).

3-Isothiocyanatopyridine can be prepared in accordance with the method described by J. C. Jochims, Chem. Ber. 101, 1746 (1968).

EXAMPLE 2

Following the procedure of Example 1, but starting from (R)-3-hydroxymethyl-N-(pyrid-3-yl)-1,2,3,4-tetrahydroisoquinoline-2-carbothioamide (12 g.) in 6N hydrochloric acid (150 cc.), (R)-3-ylimino)-1,5,10,10a-tetrahydrothiazolo[3,4-b]isoquinoline (6.8 g.), melting at 112° C., is obtained.

$[\alpha]_D^{20} = +260 \pm 3°$ ($c = 2$, ethanol).

(R)-3-Hydroxymethyl-N-(pyrid-3-yl)-1,2,3,4-tetrahydroisoquinoline-2-carbothioamide [melting point 196° C.; $[\alpha]_D^{20} = -55 \pm 1°$ (c = 2, dimethylformamide)] employed as starting material can be prepared from (R)-3-hydroxymethyl-1,2,3,4-tetrahydroisoquinoline by working under the conditions described in Example 1.

(R)-3-Hydroxymethyl-1,2,3,4-tetrahydroisoquinoline [melting point 116° C; $[\alpha]_D^{20} = +94 \pm 1°$ (c = 2, ethanol)] can be prepared from D-phenylalanine in accordance with the method of S. Yamada and T. Kunieda, Chem. Pharm. Bull., 15, 490 (1967), described for L-phenylalanine.

EXAMPLE 3

Following the procedure of Example 1, but starting from (R,S)-3-hydroxmethyl-N-(pyrid-3-yl)-1,2,3,4-tetrahydroisoquinoline-2-carbothioamide (115 g.) in 6N hydrochloric acid (1.4 liters), (R,S)-3-(pyrid-3-ylimino)-1,5,10,10a-tetrahydrothiazolo[3,4-b]isoquinoline (76 g.), melting at 110° C., is obtained.

(R,S)-3-Hydroxymethyl-N-(pyrid-3-yl)-1,2,3,4-tetrahydroisoquinoline-2-carbothioamide [instantaneous melting point: 180° C.] employed as starting material can be prepared from (R,S)-3-hydroxymethyl-1,2,3,4-tetrahydroisoquinoline by working under the conditions described in Example 1 for the preparation of (S)-3-hydroxymethyl-N-(pyrid-3-yl)-1,2,3,4-tetrahydroisoquinoline-2-carbothioamide.

(R,S)-3-Hydroxymethyl-1,2,3,4-tetrahydroisoquinoline can be prepared in accordance with the method of E. Schipper et al., J. Med. Pharm. Chem., 4, 79 (1961), from DL-phenylalanine.

EXAMPLE 4

(R,S)-6-Fluoro-3-hydroxymethyl-N-(pyrid-3-yl)-1,2,3,4-tetrahydroisoquinoline-2-carbothioamide (19 g.) and 6N hydrochloric acid (240 cc.) are heated at 65° C. for 1 hour. The reaction mixture is cooled to 0° C and is rendered alkaline by adding 10N sodium hydroxide solution. The mixture is extracted three times with methylene chloride (total 450 cc.). The organic phase is dried over sodium sulphate, filtered and concentrated to dryness under reduced pressure (25 mm. Hg) at 40° C. The residue obtained is recrystallised from acetonitrile to give (R,S)-8-fluoro-3-(pyrid-3-ylimino)-1,5,10,10a-tetrahydrothiazolo[3,4-b]isoquinoline (14 g.), melting at 139° C.

(R,S)-6-Fluoro-3-hydroxymethyl-N-(pyrid-3-yl)-1,2,3,4-tetrahydroisoquinoline-2-carbothioamide employed as starting material can be prepared in the following manner:

3-Isothiocyanatopyridine (15 g.) is added over the course of 5 minutes, at a temperature of about 15° C., to a solution of (R,S)-6-fluoro-3-hydroxymethyl-1,2,3,4-tetrahydroisoquinoline (20 g.) in ethanol (250 cc.). The temperature rises gradually to 25° C. and a white precipitate then forms. The mixture is stirred for 20 hours at 20° C. and the precipitate is then filtered off. After washing with diethyl ether (40 cc.) and drying, (R,S)-6-fluoro-3-hydroxymethyl-N-(pyrid-3-yl)-1,2,3,4-tetrahydroisoquinoline-2-carbothioamide (34 g.) is obtained in the form of white crystals melting at 190° C.

(R,S)-6-Fluoro-3-hydroxymethyl-1,2,3,4-tetrahydroisoquinoline can be prepared in the following manner:

Sodium borohydride (46 g.) dissolved in water (280 cc.) and ethanol (280 cc.) is added to (R,S)-3-ethoxycarbonyl-6-fluoro-1,2,3,4-tetrahydroisoquinoline hydrochloride (79 g.) dissolved in water (280 cc.) and ethanol (280 cc.). The reaction mixture is then stirred for 20 hours at a temperature of about 20° C. The mixture is concentrated to dryness under reduced pressure (25 mm. Hg) at 40° C. The residue is taken up in water (500 cc.) and extracted 3 times with methylene chloride (total 500 cc.). After filtering off a small amount of insoluble matter, the organic extracts are dried over sodium sulphate, filtered and then concentrated to dryness under reduced pressure (25 mm. Hg) at 40° C. By recrystallising the residue from acetonitrile, (R,S)-6-fluoro-3-hydroxymethyl-1,2,3,4-tetrahydroisoquinoline (27 g.) is obtained in the form of white crystals melting at 121° C.

The hydrochloride of (R,S)-3-ethoxycarbonyl-6-fluoro-1,2,3,4-tetrahydroisoquinoline can be prepared in accordance with the method described in the Japanese Patent Application published under No. 73/07,115.

EXAMPLE 5

(R,S)-6,7-Methylenedioxy-3-hydroxymethyl-N-(pyrid-3-yl)-1,2,3,4-tetrahydroisoquinoline-2-carbothioamide (33.6 g.) and 6N hydrochloric acid (336 cc.) are heated at 100° C for 90 minutes. The reaction mixture is cooled to 0° C, rendered alkaline by adding potassium carbonate and extracted with methylene chloride (5 × 500 cc.). After filtering off a yellow insoluble material, the combined organic extracts are dried over anhydrous potassium carbonate and then concentrated to dryness under reduced pressure (25 mm. Hg) at 40° C. This gives crystals (11.45 g.) melting at 191° C. After two recrystallisations from a mixture of acetonitrile and dimethylformamide (7:1 by volume), (R,S)-7,8-methylenedioxy-3-(pyrid-3-ylimino)-1,5,10,10a-tetrahydrothiazolo[3,4-b]isoquinoline (4.5 g.) is isolated in the form of pale yellow crystals melting at 201° C.

(R,S)-6,7-Methylenedioxy-3-hydroxymethyl-N-(pyrid-3-yl)-1,2,3,4-tetrahydroisoquinoline-2-carbothioamide employed as starting material can be prepared in the following manner:

3-Isothiocyanatopyridine (15 g.) is added over the course of a few minutes, at 27° C, to a solution of (R,S)-6,7-methylenedioxy-3-hydroxymethyl-1,2,3,4-tetrahydroisoquinoline (20.7 g.) in ethanol (400 cc.). The temperature rises to 37° C. and a white precipitate then forms rapidly. After stirring for 20 hours at a temperature of about 20° C., the precipitate is filtered off. (R,S)-6,7-Methylenedioxy-3-hydroxymethyl-N-(pyrid-3-yl)-1,2,3,4-tetrahydroisoquinoline-2-carbothioamide (34 g.) is thus isolated in the form of pale yellow crystals melting at 212° C.

(R,S)-6,7-Methylenedioxy-3-hydroxymethyl-1,2,3,4-tetrahydroisoquinoline can be prepared in the following manner:

(R,S)-6,7-Methylenedioxy-3-ethoxycarbonyl-1,2,3,4-tetrahydroisoquinoline hydrochloride (115 g.) dissolved in water (550 cc.) and ethanol (550 cc.) is added to sodium borohydride (17.5 g.) dissolved in ethanol (550 cc.) and water (550 cc.), whilst maintaining the temperature at between 10° and 20° C. The mixture is stirred for 30 minutes at about 20° C. and is then heated under reflux for 3 hours. The reaction mixture is concentrated to dryness under reduced pressure (25 mm Hg). The residue is taken up in water (1,000 cc. ) and methylene chloride (600 cc.). An insoluble material is filtered off and dried. After decanting the filtrate, the aqueous phase is extracted three times with methylene chloride (total 600 cc.). The organic extracts are combined and dried over potassium carbonate, and then concentrated to dryness under reduced pressure (25 mm. Hg) at 40° C. A product (5 g.) melting at 144° C. is thus obtained. Recrystallisation, from ethyl acetate, of this solid and of the insoluble material isolated by filtration, results in the isolation of (R,S)-6,7-methylenedioxy-3-hydroxymethyl-1,2,3,4-tetrahydroisoquinoline (49.9 g.) in the form of white crystals melting at 144° C.

The hydrochloride of (R,S)-6,7-methylenedioxy-3-ethyoxycarbonyl-1,2,3,4-tetrahydroisoquinoline can be prepared in accordance with H. Kato et al., Chem. Pharm. Bull. 21, 2043 (1973).

EXAMPLE 6

A solution of (S)-3-3-hydroxymethyl-N-(isoquinol-5-yl)-1,2,3,4-tetrahydroisoquinoline-2-carbothioamide (1.3 g.) in 6N hydrochloric acid (20 cc.) is heated at 100° C. for 1 hour. After cooling, the solution is concentrated to one-third of its volume under reduced pressure (40 mm. Hg) at 60° C., rendered alkaline by adding 10N sodium hydroxide solution (5 cc.) and then extracted with methylene chloride (3 × 25 cc.). The organic extracts are combined and then dried over magnesium sulphate. After filtration, and concentration of the filtrate to dryness under reduced pressure (25 mm. Hg) at 40° C., (S)-3-(isoquinol-5-ylimino)-1,5,10,10a-tetrahydrothiazolo-[3,4-b]isoquinoline (0.8 g.) is obtained in the form of light beige crystals melting at 164° C.

$[\alpha]_D^{20} = -197 \pm 2.5°$ (c = 2, chloroform)

(S)-3-Hydroxymethyl-N-(isoquinol-5-yl)-1,2,3,4-tetrahydroisoquinoline-2-carbothioamide employed as starting material can be pepared in the following manner:

5-Isothiocyanatoisoquinoline (0.93 g.) is added to a solution of (S)-3-hydroxymethyl-1,2,3,4-tetrahydro isoquinoline (0.82 g.) in ethanol (10 cc.). After 15 hours at a temperature of about 20° C., the crystals formed are filtered off, washed with ethanol and then dried at 60° C. under reduced pressure (0.1 mm. Hg). (S)-3-Hydroxymethyl-N-(isoquinol-5-yl)-1,2,3,4-tetrahydroisoquinoline-2-carbothioamide (1.3 g. ), melting at 190° C., is thus obtained.

5-Isothiocyanatoisoquinoline can be prepared in the following manner:

A solution of 5-aminoisoquinoline (14.4 g.) in pyridine (40 cc.) is added dropwise to a solution of triethylamine (10.1 g.) and carbon disulphide (40 cc.) in pyridine (20 cc.), whilst stirring at a temperature of about −10° C. After 1 hour at this temperature, a solution of N,N'-dicyclohexylcarbodiimide (20.6 g.) in pyridine (20 cc.) is added dropwise. Stirring is continued for 3 hours at a temperature changing from −10° to 20° C . and then for 20 hours at a temperature of about 20° C. The N,N'-dicyclohexylthiourea formed is filtered off and washed with methylene chloride (50 cc.); the filtrate is evaporated to dryness under reduced pressure (20 mm. Hg) at 40° C. The solid residue is taken up in methylene chloride (100 cc.); the new insoluble material is filtered off and washed with methylene chloride (30 cc.); the filtrate is evaporated to dryness under reduced pressure (20 mm. Hg) at 40° C. The residue is dissolved in boiling acetonitrile (100 cc.); after cooling, the crystals formed are filtered off and then suspended in diisopropyl ether (180 cc.). After 30 minutes'stirring at a temperature of about 20° C, the insoluble material is filtered off. The filtrate is evaporated to dryness under reduced pressure (20 mm. Hg) at 50° C. The residue is crystalline beige solid (5.9 g.) consisting of 5-isothiocyanatoisoquinoline, melting at 99° C. after recrystallisation from acetonitrile (40 cc.) and at 102° C. after sublimation at 70° C under reduced pressure (1 mm. Hg).

EXAMPLE 7

A suspension of 3-aminopyridine (0.5 g.) in acetonitrile (10 cc.) is added slowly, whilst stirring, to a suspension of (S)-3-chloro -1,5,10,10a-tetrahydrothiazolo[3,4-b]isoquinolinium chloride (1.3 g.) in acetonitrile (15 cc.), and triethylamine (2.9 cc.) in acetonitrile (5 cc.) is then added dropwise. It is found that there is a slight rise in the temperature of the reaction mixture, the suspension dissolves partially, and a precipitate then forms. The reaction mixture is stirred for 2 hours at a temperature of about 20° C. and is then evaporated under reduced pressure (25 mm. Hg) at 50° C. The residue is dissolved in a mixture consisting of water (25 cc.) and methylene chloride (50 cc.). The decanted organic phase is extracted with N hydrochloric acid (2 × 30 cc.). The aqueous extracts are combined, rendered alkaline by adding 10N sodium hydroxide solution, and then extracted with methylene chloride (2 × 30 cc.). The organic phase is washed with water and then dried over magnesium sulphate. After filtration, and concentration to dryness under reduced pressure (25 mm. Hg), (S)-3-(pyrid-3-ylimino-1,5,10,10a-tetrahydrothiazolo[3,4-b]isoquinoline (0.5 g.), which after recrystallisation from a mixture of benzene and diisopropyl ether (1:3 by volume), melts at 111° C ., is obtained.

$[\alpha]_D^{20} = -260 \pm 7°$ (c = 2; ethanol). (S)-3-Chloro-1,5,10,10a-tetrahydrothiazolo[3,4-b]-isoquinolinium chloride employed as starting material can be prepared in the following manner:

A solution (20 cc.) containing 2 mols per liter of phosgene in toluene, is added dropwise, in the absence of moisture, whilst stirring and at a temperature of about 20° C ., to a solution of (S)-1,5,10,10a-tetrahydrothiazolo[3,4-b]isoquinoline-3-thione (2.2 g.) in tetrahydrofuran (25 cc.). The mixture becomes cloudy after 15 minutes; it is stirred for 5 hours and then heated to 50° C. for 1 hour. The solvents are evaporated under reduced pressure (25 mm. Hg ) at 60° C. to give (S)-3-chloro-1,5,10,10a-tetrahydrothiazolo[3,4-b]isoquinolinium chloride (2.6 g.) in the form of a very hygroscopic white crystalline powder.

(S)-1,5,10,10a-Tetrahydrothiazolo[3,4-b]isoquinoline-3-thione employed as starting material can be prepared in the following manner:

Carbon disulphide (40 g.) is added dropwise at 20° C., with vigorous stirring, to a solution of (S)-3-hydroxysulphonyloxymethyl-1,2,3,4-tetrahydroisoquinoline (100 g) in 0.25N sodium hydroxide solution (4,000 cc.). The reaction is exothermic. A solid precipitates and the reaction mixture then sets solid. Stirring is continued for 3 hours. The reaction mixture is neutralised by adding 4N hydrochloride acid. The crystals formed are filtered off, washed copiously with water and then recrystallised from ethanol (3,000 cc.) to give (S)-1,5,10,10a-tetrahydrothiazolo[3,4-b]-isoquinoline-3-thione (77 g. ) in the form of fine white needles melting at 150° C.

$[\alpha]_D^{20} = -377 \pm 4°$ (c = 1; chloroform).

(S)-3-Hydroxysulphonyloxymethyl-1,2,3,4-tetrahydroisoquinoline can be prepared in the following manner:

A solution of (S)-3-hydroxymethyl-1,2,3,4-tetrahydroisoquinoline (41 g.) in a mixture of sulphuric acid ( d = 1.83; 13 cc.) and water (70 cc.) is heated at 110° C. Water (about 50 cc.) is distilled off and the mixture is then concentrated under reduced pressure (20 mm. Hg) at 100° C. The brown oily residue is taken up in a mixture of sulphuric acid (d = 1.83; 13 cc. ) and water (70 cc.); water (50 cc.) is again distilled off and the mixture is then concentrated as previously described, after which the concentration is finished at 100° C. under reduced pressure (1 mm. Hg). The residue, which crystallises on cooling, is recrystallised from a mixture of ethanol (140 cc.) and water (60 cc.) After cooling for 15 hours at about 5° C., the crystals which have appeared are filtered off and washed with a mixture of ethanol and water (3:1 by volume) (20 cc.) and then with ethanol (2 × 25 cc.). After drying at 60° C. under reduced pressure (1 mm. Hg), (S)-3-hydroxysulphonyloxymethyl-1,2,3,4-tetrahydroisoquinoline (48 g.) is obtained in the form of white crystals.

$[\alpha]_D^{20} = -55 \pm 1°$ (c = 1; dimethylsulphoxide).

EXAMPLE 8

Following the procedure of Example 7, but starting from (S)-3-chloro-1,5,10,10a-tetrahydrothiazolo[3,4-b]isoquinolinium chloride (7.8 g.) and 4-aminopyridine (3 g.), (S)-3-(pyrid-4-ylimino)-1,5,10,10a-tetrahydrothiazolo[3,4-b]isoquininoline (2.5 g.) is obtained, which melts at 110°–115° C., and, after recrystallisation from a mixture of toluene and diisopropyl ether, melts at 130° C.

$[\alpha]_D^{20} = -258 \pm 3°$ (c = 1; ethanol).

EXAMPLE 9

(S)-3-Methylthio-1,5,10,10a-tetrahydrothiazolo[3,4-b]isoquinolinium iodide (36.3 g.) is added, a little at a time, to a solution of 3-aminopyridine (15 g.) in pyridine (1 liter). The suspension gradually passes into solution. After 24 hours at a temperature of about 20° C., the solution is concentrated to dryness under reduced pressure (25 mm. Hg.). The residue is dissolved in a mixture of methylene chloride (250 cc.), 2N sodium hydroxide solution (200 cc.) and water (200 cc.). The organic phase is decanted, dried over magnesium sulphate, filtered and then concentrated under reduced pressure (30 mm. Hg) at 40° C. The residue is recrystallised from acetonitrile (150 cc.) to give (S)-3-(pyrid-3-ylimino)-1,5,10,10a-tetrahydrothiazolo[3,4-b]isoquinoline (22.4 g.) in the form of white crystals which melt at 111° C.

$[\alpha]_D^{20} = -258 \pm 3°$ (c = 2; ethanol).

(S)-3-Methylthio-1,5,10,10a-tetrahydrothiazolo[3,4-b]isoquinolinium iodide employed as starting material can be prepared in the following manner:

(S)-1,5,10,10a-Tetrahydrothiazolo[3,4-b]isoquinoline-3-thione (38 g.) is dissolved in methyl iodide (500 cc.). After 15 hours at a temperature of about 20° C., the crystals which have appeared are filtered off, washed with diethylether (2 × 50 cc.) and then dried at 20° C. under reduced pressure (1 mm. Hg) to give (S)-3-methylthio-1,5,10,10a-tetrahydrothiazolo[3,4-b]isoquinolinium iodide (61.5 g.) melting at 140°–150° C. with decomposition.

EXAMPLE 10

(S)-3-Methylthio-1,5,10,10a-tetrahydrothiazolo[3,4-b]isoquinolinium iodide (14.5 g.) is added, a little at a time, to a solution of 4-aminopyridine (7.5 g.) in pyridine (300 cc.). The suspension gradually passes into solution. After 24 hours at a temperature of about 20° C., the suspension is concentrated to dryness under reduced pressure (25 mm. Hg). The residue is dissolved in a mixture of methylene chloride (250 cc.) and water (200 cc.). The organic phase is decanted, dried over magnesium sulphate, filtered and then concentrated to about 100 cc. under reduced pressure. This solution is poured onto a column (column diameter: 3 cm) of silica gel (300 g.) and elution is then carried out with a 1% v/v solution of methanol in methylene chloride, eluate fractions of 500 cc. being collected. After evaporating fractions 2 and 3 to dryness, (S)-1,5,10,10a-tetrahydrothiazolo[3,4-b]isoquinoline-3-thione (2.0 g.) is obtained.

Fractions 6 to 9 are combined and evaporated to dryness to give (S)-3-(pyrid-4-ylimino)-1,5,10,10a-tetrahydrothiazolo[3,4-b]isoquinoline (5.1 g.) in the form of white crystals which, after recrystallisation from a mixture of toluene and diisopropyl ether (1:3 by volume), melt at 130° C.

$[\alpha]_D^{20} = -259 \pm 3°$ (c = 1; ethanol).

EXAMPLE 11

(S)-3-Methylthio-9-nitro-1,5,10,10a-tetrahydrothiazolo[3,4-b]isoquinolinium iodide (6 g.) is added to a solution of 3-aminopyridine (3 g.) in pyridine (100 cc.). After 6 hours at a temperature of about 20° C., the mixture is concentrated to dryness under reduced pressure (25 mm. Hg). The residue is dissolved in a mixture consisting of methylene chloride (300 cc.) and water (200 cc.). The organic phase is decanted, washed with water (3 × 200 cc.), dried over magnesium sulphate, filtered and then concentrated to dryness. The residue obtained is recrystallised from acetonitrile (40 cc.) to give (S)-9-nitro-3-(pyrid-3-ylimino)-1,5,10,10a-tetrahydrothiazolo[3,4-b]isoquinoline (3.9 g.) in the form of white crystals melting at 144° C.

$[\alpha]_D^{20} = -540 \pm 5°$ C (c = 2; chloroform). (S)-3-Methylthio-9-nitro-1,5,10,10a-tetrahydrothiazolo[3,4-b]isoquinolinium iodide employed as starting material can be prepared in the following manner:

(S)-9-Nitro-1,5,10,10a-tetrahydrothiazolo[3,4-b]isoquinoline-3-thione (40 g.) is dissolved in methyl iodide (100 cc.). After 48 hours at a temperature of about 20° C., the crystals which have appeared are filtered off, washed with diethyl ether (2 × 30 cc.) and then dried at 20° C under reduced pressure (1 mm. Hg). (S)-3-Methylthio-9-nitro-1,5,10,10a-tetrahydrothiazolo[3,4-b]isoquinolinium iodide (6.0 g.) is thus obtained.

(S)-7-, -8- and -9-Nitro-1,5,10,10a-tetrahydrothiazolo[3,4-b]isoquinoline-3-thiones can be prepared in the following manner:

Finely powdered anhydrous sodium nitrate (85 g.) is added to a solution of (S)-3-hydroxysulphonyloxymethyl1,2,3,4-tetrahydroisoquinoline (122 g.) in trifluoroacetic acid (1,000 cc.). The reaction mixture is stirred for 5 days at a temperature of about 20° C. and is then evaporated under reduced pressure (25 mm. Hg, followed by 1 mm. Hg). The residue is washed with diethyl ether (3 × 200 cc.). The light yellow solid obtained is ground and then dried at 40° C. under reduced pressure (1 mm.Hg). The solid thus obtained is dissolved in 0.3N sodium hydroxide solution (5,000 cc.); carbon disulphide (35 cc.) is added to the solution obtained, whilst stirring, and the stirring is continued at a temperature of about 20° C. for 17 hours. The mixture is neutralised by adding 4N hydrochloric acid. The precipitate formed is filtered off, washed copiously with water and then with ethanol, dried under reduced pressure (0.1 mm. Hg) and then dissolved in boiling toluene (3,200 cc.). The insoluble matter is filtered off over Celite and the filtrate is cooled to about 10° C. The crystals which have appeared are filtered off, washed with ethanol (100 cc.), dried at 80° C. under reduced pressure (0.1 mm. Hg) and recrystallised from a mixture of acetonitrile and ethanol (1:1 by volume) (1,000 cc.). (S)-7-Nitro-1,5,10,10a-tetrahydrothiazolo[3,4-b]isoquinoline-3-thione (45 g.) melting at 182° C., is obtained.

$[\alpha]_D^{20} = -458 \pm 5°$ (c = 2; chloroform).

The toluene filtrate is concentrated to dryness; the residue is dissolved in boiling acetonitrile (600 cc.). The insoluble matter is filtered off over Celite and the filtrate is then cooled. The crystals which have appeared are filtered off and dried under reduced pressure (0.1 mm. Hg) at 60° C. A mixture of (S)-8-nitro- and -9-nitro-1,5,10,10a-tetrahydrothiazolo[3,4-b]isoquinoline-3-thione (29 g.) is obtained. The two products are separated by chromatography on silica gel (2.4 kg) contained in a column of 7 cm diameter, elution being carried out with a mixture of methylene chloride and cyclohexane (4:1 by volume) and eluate fractions of 1,000 cc. being collected.

Fractions 6 to 15 are combined and evaporated to dryness. The residue is recrystallised from anisole (150 cc.) and then from acetonitrile (150 cc.). After drying at 60° C. under reduced pressure (0.1 mm. Hg), (S)-9-nitro-1,5,10,10a-tetrahydrothiazolo[3,4-b]isoquinoline-3-thione (6.2 g.) melting at 203° C. is obtained.

$[\alpha]_D^{20} = -654 \pm 7°$ (c = 1; chloroform).

Fractions 17 to 26 are combined and evaporated to dryness under reduced pressure (30 mm. Hg). The residue is recrystallised from anisole (170 cc.) and then from acetonitrile (170 cc.). After drying at 60° C. under reduced pressure (0.1 mm. Hg), (S)-8-nitro-1,5,10,10a-tetrahydrothiazolo[3,4-b]isoquinoline-3-thione (3.9 g.) melting at 220° C. is obtained.

$[\alpha]_D^{20} = -338 \pm 3°$ (c = 0.5; chloroform).

EXAMPLE 12

5-Aminoisoquinoline (10.8 g.) is added to a solution of (S)-3-methylthio-1,5,10,10a-tetrahydrothiazolo[3,4-b]isoquinolinium iodide (18.2 g.) in pyridine (500 cc.). After 5 hours at a temperature of about 20° C., solution is complete and the reaction is allowed to continue for 10 hours. The solution is concentrated to dryness under reduced pressure (25 mm.Hg) at 60° C. The residue is dissolved in a mixture consisting of N sodium hydroxide solution (250 cc.) and methylene chloride (250 cc.). The organic phase is decanted, washed with water (2 × 100 cc.), dried over magnesium sulphate, filtered and then concentrated to dryness under reduced pressure (50 mm.Hg) at 40° C. Isopropanol (150 cc.) is added to the residue obtained; the mixture is brought to the boil and is filtered hot. After cooling to 5° C., the crystals formed and filtered off and washed with isopropanol (3 × 10 cc.). After drying at 60° C., under reduced pressure (0.1 mm.Hg), (S)-3-(isoquinol-5-ylimino)-1,5,10,10a-tetrahydrothiazolo[3,4-b] isoquinoline (13.0 g.) is obtained in the form of white crystals melting at 164° C.

$[\alpha]_D^{20} = -198 \pm 2.5°$ (c = 2; chloroform).

EXAMPLE 13

Following the procedure of Example 12, but starting from (R)-3-methylthio-1,5,10,10a-tetrahydrothiazolo[3,4-b]isoquinolinium iodide (32.6 g.) and 5-aminoisoquinoline (21.6 g. (R)-3-(isoquinol-5-ylimino)-1,5,10,10a-tetrahydrothiazolo[3,4-b]isoquinoline (27.4 g.), melting at 164° C., after recrystallisation from acetonitrile, is obtained.

$[\alpha]_D^{20} = +199 \pm 2.5°$ (c = 2; chloroform). (R)-3-Methylthio-1,5,10,10a-tetrahydrothiazolo[3,4-b]isoquinolinium iodide employed as starting material can be prepared in the following manner:

(R)-1,5,10,10a-Tetrahydrothiazolo[3,4-b]isoquinoline-3-thione (30.0 g.) is dissolved in a mixture of methyl iodide (13 cc.) and methylene chloride (150 cc.). After 20 hours at a temperature of about 20° C., the crystals formed are filtered off, washed with diethyl ether (2 × 50 cc.) and then dried at 20° C., under reduced pressure (20 mm.Hg). This gives (R)-3-methylthio-1,5,10,10a-tetrahydrothiazolo[3,4-b]isoquinolinium iodide (38.5 g.) melting at 140°–150° C., with decomposition.

(R)-1,5,10,10a-Tetrahydrothiazolo[3,4-b]isoquinoline-3-thione can be prepared in the following manner:

Carbon disulphide (14 g.) is added dropwise, with vigorous stirring, to a solution of (R)-3-hydroxysulphonyloxymethyl-1,2,3,4-tetrahydroisoquinoline (33.9 g.) in 0.6N sodium hydroxide solution (1,000 cc.). After one hour at a temperature of about 20° C., a precipitate appears; stirring is continued for 15 hours. The mixture is neutralised by adding 4N hydrochloric acid. The crystals formed are filtered off and washed with water and then with ethanol. (R)-1,5,10,10a-Tetrahydrothiazolo[3,4-b]isoquinoline-3-thione (30.0 g.) is thus obtained in the form of white crystals melting at 150° C.

(R)-3-Hydroxysulphonyloxymethyl-1,2,3,4-tetrahydroisoquinoline can be prepared in the following manner:

A solution of (R)-3-hydroxymethyl-1,2,3,4-tetrahydroisoquinoline (22.8 g.) in a mixture of sulphuric acid (d = 1.83; 7.9 cc.) and water (50 cc.) is concentrated for 1 hour at 100° C., under reduced pressure (20 mm.Hg) and then for 1 hour at 160° C. The residue crystallises on cooling. (R)-3-Hydroxysulphonyloxymethyl-1,2,3,4-tetrahydroisoquinoline (33.9 g.) is thus obtained in the form of a white crystalline mass melting at 318° C.

(R)-3-Hydroxymethyl-1,2,3,4-tetrahydroisoquinoline can be prepared from D-phenylalanine in accordance with the method of S. Yamada and T. Kunieda, Chem. Pharm. Bull., 15, 490 (1967), described for L-phenylalanine.

EXAMPLE 14

A solution of sodium nitrite (3.1 g.) in distilled water (10 cc.) is added slowly to a solution, at 0° C., of (S)-7-amino-3-(pyrid-3-ylimino)-1,5,10,10a-tetrahydrothiazolo[3,4-b]isoquinoline (13 g.) in 4N hydrochloric acid (25 cc.). The mixture is stirred for 15 minutes at 0° C., and the solution obained is then added to a suspension of cuprous chloride (6 g.) in concentrated hydrochloric acid (d = 1.18; 25 cc.). The mixture is allowed to return to 20° C., and is then heated for 30 minutes at 70° C. After cooling to 20° C., distilled water (200 cc.), methylene chloride (250 cc.) and then N sodium hydroxide solution (100 cc.) are added. After filtration, the organic phase is recovered by decanting and is dried over magnesium sulphate, filtered and concentrated to dryness at 40° C., under reduced pressure (20 mm.Hg). The residue obtained is purified by chromatography on silica gel (200 g.) contained in a column of 3 cm. diameter, elution being carried out with methylene chloride containing 1% v/v of methanol (5,000 cc.), and 1 litre fractions being collected. Fractions 2 to 4 are combined and then concentrated to dryness. The residue obtained is recrystallised from a mixture of isopropanol (70 cc.) and heptane (100 cc.). (S)-7-Chloro-3-(pyrid-3-ylimino)-1,5,10,10a-tetrahydrothiazolo[3,4-b]isoquinoline (5.5 g.), melting at 125° C., is thus obtained.

$[\alpha]_D^{20} = -273 \pm 3°$ (c = 1.1; chloroform).

(S)-7-Amino-3-(pyrid-3-ylimino)-1,5,10,10a-tetrahydrothiazolo[3,4-b]isoquinoline employed as starting material can be prepared in the following manner:

Tin powder (6.5 g.) is added to a solution of (S)-7-nitro-3-(pyrid-3-ylimino)-1,5,10,10a-tetrahydrothiazolo[3,4-b]isoquinoline (3.3 g.) in 6N hydrochloric acid (100 cc.) and the reaction mixture is stirred for 15 hours at 20° C. After dilution with water (200 cc.) and rendering alkaline by adding 10N sodium hydroxide solution (65 cc.), the mixture is extracted with methylene chloride (3 × 150 cc.) The organic extracts are combined, washed with water (200 cc.), dried over magnesium sulphate, filtered and concentrated to dryness. The residue is recrystallised from acetonitrile (90 cc.). After drying at 60° C., under reduced pressure (0.1 mm.Hg), (S)-7-amino-3-(pyrid-3-ylimino)-1,5,10,10a-tetrahydrothiazolo[3,4-b]isoquinoline (2.2 g.) melting at 191° C., is obtained $[\alpha]_D^{20} = -245 \pm 3°$ (c = 2; chloroform).

(S)-7-Nitro-3-(pyrid-3-ylimino)-1,5,10,10a-tetrahydrothiazolo[3,4-b]isoquinoline can be prepared in accordance with one or other of the following methods;

a. A solution of (S)-3-hydroxymethyl-7-nitro-N-(pyrid-3-yl)-1,2,3,4-tetrahydroisoquinoline-2-carbothioamide (0.344 g.) in 6N hydrochloric acid (4 cc.) is heated for 30 minutes at 50° C. The reaction mixture is then poured into distilled water (100 cc.) and is rendered alkaline, to pH 12, by adding 4N sodium hydroxide solution. The mixture is extracted with methylene chloride (3 × 50 cc.) and the extracts are dried over potassium carbonate and concentrated to dryness under reduced pressure (30 mm.Hg) at 40° C. (S)-7-Nitro-3-(pyrid-3-ylimino)-1,5,10,10a-tetrahydrothiazolo[3,4-b]isoquinoline (0.200 g.) is obtained in the form of yellow crystals having the same characteristics as the product described in connection with method (b) below.

(S)-3-Hydroxymethyl-7-nitro-N-(pyrid-3-yl)-1,2,3,4-tetrahydroisoquinoline-2-carbothioamide can be prepared in the following manner:

3-Isothiocyanatopyridine (0.272 g.) is added to a suspension of (S)-3-hydroxymethyl-7-nitro-1,2,3,4-tetrahydroisoquinoline (0.416 g.) in absolute ethanol (10 cc.). After 3 minutes, the mixture becomes homogeneous, and a pale yellow precipitate then forms. The mixture is stirred for 1 hour at 20° C., and the precipitate is then filtered off. After drying (S)-3-hydroxymethyl-7-nitro-N-(pyrid-3-yl)-1,2,3,4-tetrahydroisoqunioline-2-carbothioamide in the form of crystals (0.575 g.) melting at 175° C., is obtained.

$[\alpha]_D^{20} = +132.6 \pm 2°$ (c = 0.5; methanol).

(S)-3-Hydroxymethyl-7-nitro-1,2,3,4-tetrahydroisoquinoline can be prepared in the following manner:

Sodium borohydride (8.4 g.) dissolved in ethanol (56 cc.) and distilled water (56 cc.) is added, whilst stirring at a temperature of about 20° C., to a suspension of (S)-3-ethoxycarbonyl-7-nitro-1,2,3,4-tetrahydroisoquinoline (14 g.) in ethanol (56 cc.) and distilled water (56 cc.). After stirring for 1 hour at about 20° C., the mixture becomes homogeneous and then deposits a precipitate after a further 30 minutes. It is left at 20° C., for about 1 hour and the ethanol is then distilled under reduced pressure (30 mm.Hg). The residue is taken up in distilled water (250 cc.) and is extracted with methylene chloride (3 × 50 cc.). The organic extracts are dried over potassium carbonate, filtered and concentrated to dryness under reduced pressure (30 mm.Hg) at 40° C. An orange solid is obtained, which is recrystallised from acetonitrile (100 cc.). After drying, (S)-3-hydroxymethyl-7-nitro-1,2,3,4-tetrahydroisoquinoline is obtained as pale yellow crystals (5 g.) melting at 184° C.

$[\alpha]_D^{20} = -73.4 \pm 1.5°$ (c = 0.5; 0.1N HCl).

(S)-3-Ethoxycarbonyl-7-nitro-1,2,3,4-tetrahydroisoquinoline can be prepared in the following manner:

3-Ethoxycarbonyl-1,2,3,4-tetrahydroisoquinoline hydrochloride (50 g.) is added in small portions, at −20° C., whilst stirring, to concentrated sulphuric acid (d = 1.83; 325 cc.). After 10 minutes, a limpid solution is obtained. The mixture is cooled to −30° C., and concentrated nitric acid (d = 1.49; 10 cc.) is then added over the course of 15 minutes. The reaction mixture is left, whilst being stirred, at −40° C., for 30 minutes and is then poured onto ice (1 kg.) and rendered alkaline by adding sodium hydroxide solution (d = 1.33; 1,000 cc.) whilst maintaining the temperature at between 15° and 20° C. The batch is extracted with methylene chloride (3 × 500 cc.). The organic extracts are combined, dried over potassium carbonate, filtered and evaporated under reduced pressure (30 mm.Hg) at 40° C. A pinkish solid (34 g.) is obtained, which is recrystallised from diisopropyl ether (300 cc.). (S)-3-Ethoxycarbonyl-7-nitro-1,2,3,4-tetrahydroisoquinoline is thus obtained in the form of pale pink crystals (17.5 g.) melting at 94°–95° C. are thus obtained.

$[\alpha]_D^{20} = -107 \pm 2°$ (c = 0.5; chloroform).

3-Ethoxycarbonyl-1,2,3,4-tetrahydroisoquinoline hydrochloride can be prepared in accordance with the method described by S. Yamada et al., Chem. Pharm. Bull. 15, 490 (1967).

b. (S)-3-Methylthio-7-nitro-1,5,10,10a-tetrahydrothiazolo[3,4-b]isoquinolinium iodide (23 g.) is added to a solution of 3-aminopyridine (11 g.) in pyridine (400 cc.). After 6 hours at a temperature of about 20° C., the mixture is concentrated to dryness under reduced pressure (25 mm.Hg). The residue is dissolved in a mixture consisting of methylene chloride (1,500 cc.) and water (500 cc.). The organic phase is decanted, washed with water (3 × 200 cc.), dried over magnesium sulphate, filtered and then concentrated to dryness. The residue obtained is recrystallised from a mixture of acetonitrile and ethanol (1:1 by volume). (S)-7-Nitro-3-(pyrid-3-ylimino)-1,5,10,10a-tetrahydrothiazolo[3,4-b]isoquinoline (16.2 g.) is thus obtained in the form of yellow crystals melting at 234° C.

$[\alpha]_D^{20} = -311 \pm 3°$ (c = 2; chloroform).

(S)-3-Methylthio-7-nitro-1,5,10,10a-tetrahydrothiazolo[3,4-b]isoquinolinium iodide employed as starting material can be prepared in the following manner:

(S)-7-Nitro-1,5,10,10a-tetrahydrothiazolo[3,4-b]isoquinoline-3-thione (16 g.) is dissolved in methyl iodide (800 cc.). After 15 hours at a temperature of about 20° C., the crystals which have appeared are filtered off, washed with diethyl ether (2 × 30 cc.) and then dried at 20° C., under reduced pressure (1 mm.Hg). (S)-3-Methylthio-7-nitro-1,5,10,10a-tetrahydrothiazolo[3,4-b]isoquinolinium iodide (23.3 g.) is thus obtained.

The preparation of (S)-7-nitro-1,5,10,10a-tetrahydrothiazolo[3,4-b]isoquinoline-3-thione has been described above, in Example 11.

EXAMPLE 15

Concentrated hydrochloric acid (d = 1.18; 12 cc.) is added to a solution, cooled to 5° C., of (S)-7-amino-3-(pyrid-3-ylimino)-1,5,10,10a-tetrahydrothiazolo[3,4-b]isoquinoline (11.8 g.) in distilled water (8 cc.). The mixture is stirred and cooled to −5° C; a solution of sodium nitrite (3.35 g.) in distilled water (8 cc.) a run in slowly whilst maintaining the temperature at between −3° and −5° C. The stirring is continued for 10 minutes, the mixture is then cooled to −10° C., and 75% w/v hexafluorophosphoric acid (15.4 g.) is added with vigorous stirring. Stirring is continued for 45 minutes at −10° C; a brown precipitate forms. The aqueous phase is removed by decantation; the brown solid is washed with a mixture (5 × 30 cc.) of diethyl ether and methanol (8:2 by volume) and is dried under reduced pressure (0.1 mm.Hg) at 20° C. This solid is added, in small portions, to boiling anhydrous xylene (150 cc.). After the end of the addition, boiling is continued for 20 minutes and the mixture is then cooled to 20° C., and a 5% w/v aqueous sodium carbonate solution (100 cc.) is added whilst stirring vigorously. The organic phase (xylene) is separated by decantation from the aqueous phase, and the brown tar in the aqueous phase which has formed in the reaction is dissolved by means of a mixture (110 cc.) of methylene chloride and methanol (90:10 by volume). The solution in methylene chloride obtained is washed with 0.1N sodium hydroxide solution (2 × 80 cc.) and then with distilled water (2 × 50 cc.); it is then combined with the above xylene solution. The combined solution is dried over magnesium sulphate, filtered and evaporated to dryness under reduced pressure (30 mm.Hg) at 70° C. The residue obtained is purified by chromatography on silica gel (120 g.) contained in a column of 2.5 cm. diameter, elution being carried out with methylene chloride containing 2% v/v of methanol (2,500 cc.), and fractions of 250 cc. being collected. Fractions 5 to 8 are combined and then concentrated to dryness. The residue obtained is crystallised from diethyl ether. This gives (S)-7-fluoro-3-(pyrid-3-ylimino)-1,5,10,10a-tetrahydrothiazolo[3,4-b]-isoquinoline (5.1 g.) melting at 99° C.

$[\alpha]_D^{20} = -227 \pm 3°$ (c = 1; methanol).

EXAMPLE 16

Sodium cyanoborohydride (7.5 g.) and acetic acid (7.5 cc) are added alternately, and in small portions, to a solution, stirred at 20° C., of (S)-7-amino-3-(pyrid-3-ylimino)-1,5,10,10a-tetrahydrothiazolo[3,4-b]isoquinoline (11.4 g.) in a mixture of an aqueous 30% w/v formaldehyde solution (30 cc.) and acetonitrile (150 cc.). The mixture is stirred for 2 hours at 20° C., and is then rendered alkaline by adding 10N sodium hydroxide solution (12 cc.). The mixture is concentrated to about 50 cc. under reduced pressure (30 mm.Hg) at 40° C. Methylene chloride (250 cc.) is added and the solution is washed with distilled water (5 × 100 cc.), dried over magnesium sulphate filtered and concentrated to dryness under reduced pressure (30 mm.Hg) at 40° C. The brown oil obtained is dissolved in 4N hydrochloric acid (250 cc.) and the solution is heated under reflux for 6 hours. It is then cooled to 4° C., rendered alkaline with 10N sodium hydroxide solution and extracted with chloroform (3 × 100 cc.). The chloroform extracts are combined, washed with water (5 × 100 cc.), dried over magnesium sulphate, filtered and concentrated to dryness under reduced pressure (30 mm.Hg) at 40° C. The residue is purified by chromatography on silica gel (200 g.) contained in a column of 3 cm. diameter, elution being carried out with methylene chloride (500 cc.) and then with methylene chloride containing 1% v/v of methanol (1 liter). The fractions corresponding to this latter eluant are combined and concentrated to dryness.

The residue obtained is recrystallised from acetonitrile. (S)-7-Dimethylamino-3-(pyrid-3-ylimino)-1,5,10,10a-tetrahydrothiazolo[3,4-b]isoquinoline (1.6 g.), melting at 138° C., is thus obtained.

$[\alpha]_D^{20} = -279 \pm 3°$ (c = 1; methanol).

EXAMPLE 17

The following are added successively to a solution, at 0° C., of copper sulphate pentahydrate (15.2 g.) in distilled water (30 cc.): a solution of potassium cyanide (16.3 g.) in distilled water (30 cc.), followed by sodium bicarbonate (33.6 g.), toluene (150 cc.) and, whilst still maintaining the temperature at 0° C., a solution obtained by mixing, at 0° C., (S)-7-amino-3-(pyrid-3-ylimino)-1,5,10,10a-tetrahydrothiazolo[3,4-b]isoquinoline (14.8 g.), distilled water (15 cc.), concentrated hydrochloric acid (d = 1.18; 20 cc.) and sodium nitrite (3.9 g.) in distilled water (20 cc.). After the end of the addition, the mixture is ketp at 0° C., for a further hour whilst stirring, is then allowed to return to 20° C., and is heated for 30 minutes at 50° C., on a water bath. It is then cooled to 20° C., and filtered, and the precipitate obtained is washed with hot toluene (3 × 100 cc.). The toluene phase is recovered by decantation, washed with N sodium hydroxide solution (2 × 200 cc.) and then with distilled water (100 cc.), dried over magnesium sulphate, filtered and concentrated to dryness under reduced pressure (30 mm.Hg) at 70° C. The residue obtained is purified by chromatography on silica gel (180 g.) contained in a column of 3 cm. diameter, elution being carried out with methylene chloride containing 0.6% v/v of methanol (7,500 cc.) and fractions of 250 cc. being collected. Fractions 11 to 30 are combined and then concentrated to dryness. The residue obtained is crystallised from ethanol. (S)-7-Cyano-3-(pyrid-3-ylimino)-1,5,10,10a-tetrahydrothiazolo[3,4-b]isoquinoline (4.8 g.), melting at 172° C., is thus obtained.

$[\alpha]_D^{20} = -300 \pm 3°$ (c =1; chloroform).

The present invention includes within its scope pharmaceutical compositions comprising, as active ingredient, at least one of the compounds of general formula I, or a non-toxic acid addition salt thereof, in association with a pharmaceutical carrier or coating. The invention includes especially such preparations made up for oral, parenteral or rectal administration or as ointments.

Solid compositions for oral administration include tablets, pills, powders and granules. In such solid compositions the active compound is admixed with at last one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration also include capsules of absorbable material such as gelatin containing the active substance with or without the addition of diluents or excipients.

Preparations accordng to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment. The compositions are particularly useful in human therapy because of their analgesic and antipyretic effects. They are particularly suitable for the treatment of acute and chronic pains, rheumatic and traumatic algias, and dental, neurological and visceral pains. In human therapy the compositions when administered to an adult should generally give doses between 50 mg. and 1000 mg. of active substance per day. In general the physician will decide the posology considered appropriate, taking into account the age and weight and other factors intrinsic to the patient being treated.

The following Examples illustrate pharmaceutical compositions according to the invention.

EXAMPLE 18

Tablets containing the active product (100 mg.) and having the following composition are prepared in accordance with the usual technique:

| | |
|---|---|
| (S)-3-(pyrid-3-ylimino)-1,5,10,10a-tetrahydrothiazolo[3,4-b]isoquinoline | 0.100 g. |
| starch | 0.110 g. |
| precipitated silica | 0.035 g. |
| magnesium stearate | 0.005 g. |

EXAMPLE 19

Tablets containing the active product (100 mg.) and having the following composition are prepared in accordance with the usual technique:

| | |
|---|---|
| (S)-3-(isoquinol-5-ylimino)-1,5,10,10a-tetrahydrothiazolo[3,4-b]isoquinoline | 0.100 g. |
| starch | 0.110 g. |
| precipitated silica | 0.035 g. |
| magnesium stearate | 0.005 g. |

We claim:

1. A thiazolo[3,4-b]isoquinoline derivative of the general formula:

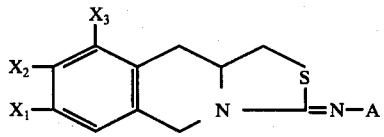

wherein A represents 3-pyridyl, 4-pyridyl or 5-isoquinolyl and, when A represents 3-pyridyl, $X_1$ represents hydrogen, halogen, dimethylamino or cyano, $X_2$ represents hydrogen or fluorine and $X_3$ represents hydrogen or nitro, at least two of $X_1$, $X_2$ and $X_3$ representing hydrogen, or $X_1$ and $X_2$ together represent methylenedioxy and $X_3$ represents hydrogen, and when A represents 4-pyridyl or 5-isoquinolyl, $X_1$, $X_2$ and $X_3$ each represent hydrogen and its nontoxic pharmaceutically acceptable acid addition salts.

2. A thiazolo[3,4-b]isoquinoline derivative according to claim 1 wherein A represents 3-pyridyl or 4-pyridyl and, when A represents 3-pyridyl, $X_1$ represents hydrogen, halogen, dimethylamino or cyano, $X_2$ represents hydrogen or fluorine and $X_3$ represents hydrogen or nitro, at least two of $X_1$, $X_2$ and $X_3$ representing hydrogen, or $X_1$ and $X_2$ together represent methylenedioxy and $X_3$ represents hydrogen, and when A represents 4-pyridyl, $X_1$, $X_2$ and $X_3$ each represent hydrogen and its non-toxic pharmaceutically acceptable acid addition salts.

3. A thiazolo[3,4-b]isoquinoline derivative according to claim 1 wherein A represents 5-isoquinolyl and $X_1$, $X_2$ and $X_3$ each represent hydrogen, and its non-toxic pharmaceutically acceptable acid addition salts.

4. A thiazolo[3,4-b]isoquinoline derivative according to claim 1 wherein A represents 3-pyridyl, 4-pyridyl or 5-isoquinolyl and $X_1$, $X_2$ and $X_3$ represent hydrogen, and its non-toxic pharmaceutically acceptable acid addition salts.

5. The thiazolo[3,4-b]isoquinoline derivative according to claim 1 which is (S)-3-(pyrid-3-ylimino)-1,5,10,10a-tetrahydrothiazolo[3,4-b]isoquinoline and non-toxic pharmaceutically acceptable acid addition salts thereof.

6. The thiazolo[3,4-b]isoquinoline derivative according to claim 1 which is (R)-3-(pyrid-3-ylimino)-1,5,10,10a-tetrahydrothiazolo[3,4-b]isoquinoline and non-toxic pharmaceutically acceptable acid addition salts thereof.

7. The thiazolo[3,4-b]isoquinoline derivative according to claim 1 which is (R,S)-3-(pyrid-3-ylimino)-1,5,10,10a-tetrahydrothiazolo[3,4-b]isoquinoline and non-toxic pharmaceutically acceptable acid addition salts thereof.

8. The thiazolo[3,4-b]isoquinoline derivative according to claim 1 which is (R,S)-8-fluoro-3-(pyrid-3-ylimino)-1,5,10,10a-tetrahydrothiazolo[3,4-b]isoquinoline and non-toxic pharmaceutically acceptable acid addition salts thereof.

9. The thiazolo[3,4-b]isoquinoline derivative according to claim 1 which is (R,S)-7,8-methylenedioxy-3-(pyrid-3-ylimino)-1,5,10,10a-tetrahydrothiazolo[3,4-b]isoquinoline and non-toxic pharmaceutically acceptable acid addition salts thereof.

10. The thiazolo[3,4-b]isoquinoline derivative according to claim 1 which is (S)-3-(isoquinol-5-ylimino)-1,5,10,10a-tetrahydrothiazolo[3,4-b]isoquinoline and non-toxic pharmaceutically acceptable acid addition salts thereof.

11. The thiazolo[3,4-b]isoquinoline derivative according to claim 1 which is (S)-3-(pyrid-4-ylimino)-1,5,10,10a-tetrahydrothiazolo[3,4-b]isoquinoline and non-toxic pharmaceutically acceptable acid addition salts thereof.

12. The thiazolo[3,4-b]isoquinoline derivative according to claim 1 which is (S)-9-nitro-3-(pyrid-3-ylimino)-1,5,10,10a-tetrahydrothiazolo[3,4-b]isoquinoline and non-toxic pharmaceutically acceptable acid addition salts thereof.

13. The thiazolo[3,4-b]isoquinoline derivative according to claim 1 which is (R)-3-(isoquinol-5-ylimino)-1,5,10,10a-tetrahydrothiazolo[3,4-b]isoquinoline and non-toxic pharmaceutically acceptable acid addition salts thereof.

14. The thiazolo[3,4-b]isoquinoline derivative according to claim 1 which is (S)-7-chloro-3-(pyrid-3-ylimino)-1,5,10,10a-tetrahydrothiazolo[3,4-b]isoquinoline and non-toxic pharmaceutically acceptable acid addition salts thereof.

15. The thiazolo[3,4-b]isoquinoline derivative according to claim 1 which is (S)-7-fluoro-3-(pyrid-3-ylimino)-1,5,10,10a-tetrahydrothiazolo[3,4-b]isoquinoline and non-toxic pharmaceutically acceptable acid addition salts thereof.

16. The thiazolo[3,4-b]isoquinoline derivative according to claim 1 which is (S)-7-dimethylamino-3-(pyrid-3-ylimino)-1,5,10,10a-tetrahydrothizolo[3,4-b]isoquinoline and non-toxic pharmaceutically acceptable acid addition salts thereof.

17. The thiazolo[3,4-b]isoquinoline derivative according to claim 1 which is (S)-7-cyano-3-(pyrid-3-ylimino)-1,5,10,10a-tetrahydrothiazolo[3,4-b]isoquinoline and non-toxic pharmaceutically acceptable acid addition salts thereof.

18. A pharmaceutical composition useful as an analgesic, antipyretic or anti-inflammatory which comprises as active ingredient an effective amount of a thiazolo[3,4-b]isoquinoline derivative of the general formula depicted in claim 1, wherein A, $X_1$, $X_2$ and $X_3$ are as defined in claim 1, or a non-toxic pharmaceutically acceptable acid addition salt thereof, in association with a significant amount of a pharmaceutically acceptable carrier.

* * * * *